(12) United States Patent
Beeby

(10) Patent No.: US 10,383,713 B2
(45) Date of Patent: Aug. 20, 2019

(54) METHOD OF MANUFACTURING AN ARTICLE

(71) Applicant: RENISHAW PLC, Wotton-under-Edge, Gloucestershire (GB)

(72) Inventor: David Beeby, Wooton-Under-Edge (GB)

(73) Assignee: RENISHAW PLC, Wotton-under-Edge (GB)

( * ) Notice: Subject to any disclaimer, the term of this patent is extended or adjusted under 35 U.S.C. 154(b) by 712 days.

(21) Appl. No.: 14/399,560

(22) PCT Filed: May 10, 2013

(86) PCT No.: PCT/GB2013/051210
§ 371 (c)(1),
(2) Date: Nov. 7, 2014

(87) PCT Pub. No.: WO2013/167904
PCT Pub. Date: Nov. 14, 2013

(65) Prior Publication Data
US 2015/0093719 A1    Apr. 2, 2015

(30) Foreign Application Priority Data

May 10, 2012 (EP) .................................. 12167523.5
May 10, 2012 (EP) .................................. 12167533.4
(Continued)

(51) Int. Cl.
*B33Y 10/00*     (2015.01)
*B23K 26/342*    (2014.01)
(Continued)

(52) U.S. Cl.
CPC ...... *A61C 13/0013* (2013.01); *A61C 13/0006* (2013.01); *A61C 13/083* (2013.01);
(Continued)

(58) Field of Classification Search
CPC ............ A16C 13/0013; A16C 13/0018; A16C 13/0019; A16C 13/008
See application file for complete search history.

(56) References Cited

U.S. PATENT DOCUMENTS 4,118,301 A   10/1978   Mayer et al.
4,801,367 A   1/1989    Burgess et al.
(Continued)

FOREIGN PATENT DOCUMENTS

CA    2295896 A1   7/2000
CN    1044308 A    8/1990
(Continued)

OTHER PUBLICATIONS

Apr. 8, 2016 Office Action issued in Chinese Patent Application No. 201380036083.3.
(Continued)

*Primary Examiner* — Jacob J Cigna
(74) *Attorney, Agent, or Firm* — Oliff PLC

(57) ABSTRACT

A method of manufacturing an article including taking an article in an initial state formed using an additive manufacturing process, the article including at least one set of mounting features; performing a second manufacturing process to transform the article into a second state, which includes mounting, via the at least one set of mounting features, the article in a holding device of a machine for operating on the article, wherein the position and orientation of the article in three linear and three rotational degrees of freedom within the machine operating volume is known and defined by virtue of the interaction of the mounting features with the holding device, and processing at least one feature on the article. The at least one mounting feature includes
(Continued)

kinematic mount features which engage with corresponding kinematic mount features on the holding device of the machine.

23 Claims, 6 Drawing Sheets

(30) Foreign Application Priority Data

| May 10, 2012 | (EP) | ................... | 12167541.7 |
|---|---|---|---|
| Jun. 7, 2012 | (GB) | ................... | 1210120.0 |
| Jun. 7, 2012 | (GB) | ................... | 1210121.8 |

(51) Int. Cl.
  *A61C 13/00* (2006.01)
  *A61C 13/083* (2006.01)
  *B33Y 80/00* (2015.01)

(52) U.S. Cl.
  CPC ........ *B23K 26/342* (2015.10); *A61C 13/0018* (2013.01); *B33Y 10/00* (2014.12); *B33Y 80/00* (2014.12); *Y10T 29/49567* (2015.01)

(56) References Cited

U.S. PATENT DOCUMENTS

| 4,826,580 | A |   | 5/1989 | Masuzawa et al. |
| 5,064,521 | A |   | 11/1991 | Stepanenko et al. |
| 5,064,731 | A |   | 11/1991 | Miyazaki et al. |
| 5,257,460 | A |   | 11/1993 | McMurtry |
| 5,647,704 | A | * | 7/1997 | Turchan .................. B23Q 3/18 269/47 |
| 5,725,376 | A |   | 3/1998 | Poirier |
| 5,813,859 | A | * | 9/1998 | Hajjar ................ A61C 13/0003 29/896.1 |
| 5,823,778 | A |   | 10/1998 | Schmitt et al. |
| 5,847,958 | A |   | 12/1998 | Shaikh et al. |
| 6,382,975 | B1 |   | 5/2002 | Poirier |
| 6,657,155 | B2 |   | 12/2003 | Abe et al. |
| 7,035,702 | B2 |   | 4/2006 | Jelonek et al. |
| 7,172,724 | B2 |   | 2/2007 | Abe et al. |
| 7,452,500 | B2 |   | 11/2008 | Uckelmann |
| 7,740,797 | B2 |   | 6/2010 | Abe et al. |
| 7,776,189 | B2 |   | 8/2010 | Shrivastava et al. |
| 8,021,154 | B2 |   | 9/2011 | Holzner et al. |
| 8,029,283 | B2 |   | 10/2011 | Schwarz et al. |
| 8,398,396 | B2 |   | 3/2013 | Taormina |
| 8,425,973 | B2 |   | 4/2013 | Dunne |
| 8,502,107 | B2 |   | 8/2013 | Uckelmann |
| 8,510,929 | B2 |   | 8/2013 | McMurtry et al. |
| 8,590,157 | B2 |   | 11/2013 | Kruth et al. |
| 8,739,409 | B2 |   | 6/2014 | Vagt et al. |
| 8,778,443 | B2 |   | 7/2014 | Uckelmann et al. |
| 8,865,033 | B2 |   | 10/2014 | Schechner et al. |
| 8,940,402 | B2 |   | 1/2015 | Giordano |
| 9,022,784 | B2 |   | 5/2015 | Johansson et al. |
| 9,283,620 | B2 |   | 3/2016 | Garcia Aparicio et al. |
| 2001/0029010 | A1 |   | 10/2001 | Wells et al. |
| 2002/0007294 | A1 |   | 1/2002 | Bradbury et al. |
| 2002/0137002 | A1 |   | 9/2002 | Bodenmiller |
| 2002/0187458 | A1 |   | 12/2002 | Dolabdjian et al. |
| 2003/0054729 | A1 |   | 3/2003 | Lee et al. |
| 2003/0207235 | A1 |   | 11/2003 | der Zel |
| 2004/0107019 | A1 |   | 6/2004 | Keshavmurthy et al. |
| 2004/0217095 | A1 |   | 11/2004 | Herzog |
| 2005/0016867 | A1 |   | 1/2005 | Kreiskott et al. |
| 2005/0060868 | A1 | * | 3/2005 | McMurtry ........... A61C 9/0093 29/559 |
| 2005/0106534 | A1 |   | 5/2005 | Gahlert |
| 2005/0173258 | A1 |   | 8/2005 | Aeby et al. |
| 2005/0186538 | A1 |   | 8/2005 | Uckelmann |
| 2006/0105297 | A1 |   | 5/2006 | Knapp et al. |
| 2006/0166500 | A1 |   | 7/2006 | Manens et al. |
| 2006/0172263 | A1 |   | 8/2006 | Quadling et al. |
| 2007/0065779 | A1 |   | 3/2007 | Mangano |
| 2007/0122767 | A1 |   | 5/2007 | Workman et al. |
| 2007/0154864 | A1 |   | 7/2007 | Deer et al. |
| 2007/0202462 | A1 |   | 8/2007 | Schwarz et al. |
| 2007/0209947 | A1 |   | 9/2007 | Shrivastava et al. |
| 2007/0256938 | A1 |   | 11/2007 | Fruth |
| 2008/0160259 | A1 |   | 7/2008 | Nielson et al. |
| 2008/0206710 | A1 |   | 8/2008 | Kruth et al. |
| 2008/0210571 | A1 |   | 9/2008 | Comaty et al. |
| 2008/0230397 | A1 |   | 9/2008 | Fecher et al. |
| 2008/0241788 | A1 |   | 10/2008 | Bauer et al. |
| 2008/0241794 | A1 |   | 10/2008 | Urata et al. |
| 2008/0241798 | A1 |   | 10/2008 | Holzner et al. |
| 2009/0068616 | A1 |   | 3/2009 | Uckelmann |
| 2009/0181346 | A1 |   | 7/2009 | Orth |
| 2009/0202378 | A1 | * | 8/2009 | Illston .................. B22F 3/1055 419/1 |
| 2009/0275000 | A1 |   | 11/2009 | Jung et al. |
| 2010/0021865 | A1 |   | 1/2010 | Uckelmann et al. |
| 2010/0143868 | A1 |   | 6/2010 | Hintersehr |
| 2010/0152872 | A1 |   | 6/2010 | Dunne et al. |
| 2010/0255441 | A1 |   | 10/2010 | Taormina |
| 2010/0291509 | A1 |   | 11/2010 | Berggren et al. |
| 2010/0310786 | A1 |   | 12/2010 | Dunne |
| 2010/0323327 | A1 |   | 12/2010 | Eriksson et al. |
| 2011/0000076 | A1 |   | 1/2011 | Mcmurtry et al. |
| 2011/0151411 | A1 |   | 6/2011 | Schechner et al. |
| 2011/0170977 | A1 |   | 7/2011 | Vagt et al. |
| 2011/0180971 | A1 |   | 7/2011 | Vagt et al. |
| 2011/0268525 | A1 | * | 11/2011 | Karpowitz ......... A61C 13/0022 409/225 |
| 2011/0316178 | A1 |   | 12/2011 | Uckelmann |
| 2012/0148985 | A1 | * | 6/2012 | Jung .................... A61C 13/08 433/212.1 |
| 2012/0202008 | A1 |   | 8/2012 | Garcia Aparicio et al. |
| 2012/0211155 | A1 |   | 8/2012 | Wehning et al. |
| 2012/0322025 | A1 |   | 12/2012 | Ozawa et al. |
| 2012/0326343 | A1 |   | 12/2012 | Eriksson et al. |
| 2014/0113248 | A1 | * | 4/2014 | Johansson .......... A61C 13/0004 433/173 |
| 2015/0093283 | A1 |   | 4/2015 | Miller et al. |
| 2015/0093720 | A1 |   | 4/2015 | Beeby et al. |
| 2015/0273757 | A1 |   | 10/2015 | Pforte et al. |

FOREIGN PATENT DOCUMENTS

| CN | 1222205 A | 7/1999 |
| CN | 1620596 A | 5/2005 |
| CN | 1889898 A | 1/2007 |
| CN | 101715325 A | 5/2010 |
| DE | 19533960 A1 | 3/1997 |
| DE | 102004009127 A1 | 9/2005 |
| DE | 102008030050 A1 | 8/2009 |
| DE | 102012108217 A1 | 12/2013 |
| EP | 1021997 A2 | 7/2000 |
| EP | 1142541 A2 | 10/2001 |
| EP | 1464298 A2 | 10/2004 |
| EP | 1764061 A1 | 3/2007 |
| EP | 1974688 A1 | 10/2008 |
| EP | 2014254 A1 | 1/2009 |
| EP | 2238941 A1 | 10/2010 |
| EP | 2489327 A1 | 8/2012 |
| GB | 1557018 | 12/1979 |
| JP | S54-99739 A | 8/1979 |
| JP | H02-213500 A | 8/1990 |
| JP | H3-111042 A | 5/1991 |
| JP | 2005515458 A | 5/2005 |
| JP | 2006-501867 A | 1/2006 |
| JP | 2007-252897 A | 10/2007 |
| SE | 1051181 A1 | 5/2012 |
| SE | 535361 C2 | 7/2012 |
| WO | 92/22785 A1 | 12/1992 |
| WO | 02/09612 A1 | 2/2002 |
| WO | 03/053274 A1 | 7/2003 |
| WO | 2005/077296 A1 | 8/2005 |
| WO | 2006/079188 A1 | 8/2006 |
| WO | 2007/103446 A2 | 9/2007 |

(56) References Cited

FOREIGN PATENT DOCUMENTS

| WO | 2008/083358 | A1 | 7/2008 | |
|---|---|---|---|---|
| WO | 2008/148495 | A1 | 12/2008 | |
| WO | 2009/073498 | A1 | 6/2009 | |
| WO | 2009/106830 | A1 | 9/2009 | |
| WO | 2009/106833 | A2 | 9/2009 | |
| WO | 2010/003882 | A2 | 1/2010 | |
| WO | 2010/039910 | A1 | 4/2010 | |
| WO | 2011/045451 | A1 | 4/2011 | |
| WO | 2011/102118 | A1 | 8/2011 | |
| WO | 2011/124474 | A1 | 10/2011 | |
| WO | 2012/064257 | A1 | 5/2012 | |
| WO | 2012/065936 | A1 | 5/2012 | |
| WO | WO 2012064257 | A1 * | 5/2012 | ......... A61C 13/0004 |
| WO | 2013/079723 | A1 | 6/2013 | |
| WO | 2013/167915 | A1 | 11/2013 | |

OTHER PUBLICATIONS

May 13, 2016 Office Action issued in Chinese Patent Application No. 201380030706.6.

Aug. 18, 2016 Office Action issued in Chinese Patent Application No. 201380030706.6.

Aug. 26, 2016 Office Action issued in Chinese Patent Application No. 201380036303.2.

Nov. 15, 2016 Office Action issued in European Patent Application No. 13722027.3.

Dec. 8, 2016 Office Action issued in Chinese Application No. 201380036083.3.

Apr. 19, 2017 Office Action issued in U.S. Appl. No. 14/399,672.

Mar. 21, 2017 Office Action issued in Japanese Patent Application No. 2015-510879.

Apr. 28, 2017 Office Action issued in Chinese Application 201380036303.2.

Apr. 4, 2017 Office Action issued in Japanese Application No. 2015-510878.

Oct. 30, 2015 Office Action issued in Chinese Patent Application No. 201380036303.2.

Aug. 20, 2015 Office Action issued in Chinese Patent Application No. 201380030706.6.

Aug. 27, 2015 Office Action issued in Chinese Patent Application No. 201380036083.3.

Jul. 31, 2017 Decision of Rejection issued in Chinese Patent Application No. 201380036083.3.

Aug. 10, 2017 Office Action issued in European Application No. 13 722 027.3.

Aug. 7, 2017 Office Action issued in European Application No. 13722516.5.

Apr. 25, 2017 Office Action issued in Japanese Patent Application No. 2015-510877.

Jun. 6, 2017 Office Action issued in European Patent Application No. 13 722 029.9.

Nov. 2, 2017 Office Action Issued in U.S. Appl. No. 14/399,754.

Oct. 16, 2017 Office Action issued in Chinese Application No. 201380036303.2.

Braddick, H.J.J. "Mechanical Design of Laboratory Apparatus". Chapman & Hall, London, pp. 5-31, 1960.

Oct. 25, 2012 Search Report and Written Opinion issued in European Patent Application No. 12167523.

Oct. 22, 2012 Search Report issued in European Patent Application No. 12167533.

Oct. 8, 2012 Search Report issued in United Kingdom Application No. 1210121.8.

Jul. 23, 2013 Search Report and Written Opinion issued in International Patent Application No. PCT/GB2013/051210.

Nov. 26, 2012 Search Report issued in European Patent Application No. 12167541.

Oct. 8, 2012 Search Report issued in United Kingdom Application No. GB1210120.0.

Aug. 8, 2013 Search Report issued in International Patent Application No. PCT/GB2013/051208.

Jul. 9, 2013 Search Report issued in International Patent Application No. PCT/GB2013/051212.

Dimov, S.S. et al. "Rapid tooling Applications of the selective laser sintering process." Assembly Automation vol. 21, pp. 296-302, 2001.

Kojima M. et al. "Injection mould with permeability utilised Metal Laser Sintering Combined with High Speed Milling." Int. J. Precision Technology, vol. 1, No. 1, 2007, pp. 55-64.

Arrizabalaga, Nicolás Larbáburu. "Máquinas. Prontuario. Técnicas máquinas herramientas." Thomson Editores, 2004, pp. 490.

Gómez. "Procedimientos de Mecanizado." Editorial Paraninfo, 2006, 2nd Edition.

Kalpakjian et al. "Manufactura Ingeniería y tecnología." 4th Edition, 2002.

Teruel. "Control numérico y programación." Ediciones técnicas, 2005.

D T Pham et al. "Selective laser sintering: applications and technological capabilities." Proceedings of the Institution of Mechanical Engineers, vol. 213 Part B, pp. 435-449, 1999.

J. P. Kruth et al. "Lasers and materials in selective laser sintering." Assembly Automation, vol. 23, No. 4, pp. 357-371, 2003.

Mahbubur et al. "Positioning accuracy improvement in five-axis milling by post processing." Int. J. Mach. Tools Manufact., vol. 37, No. 2, pp. 223-236, 1997.

J.R. Gavelis et al. "The effect of various finish line preparations on the marginal seal and occlusal seat of full crown preparations." Journal of Prosthetic Dentistry, vol. 92, No. 1, pp. 1-7, Jul. 2004.

Kruth et al. "Rapid Manufacturing of Dental Prostheses by means of Selective Laser Sintering/Melting." Proceedings of the AFPR, 2005.

Shi and Gibson. "Surface Finishing of Selective Laser Sintering Parts with Robot." Solid Freeform Fabrication (SFF) Symposium, Austin TX, 1998, pp. 27-35.

Lai and Gibson. "A Flexible Rapid Prototyping Cell." Solid Freeform Fabrication (SFF) Symposium, Austin TX, 2000, pp. 275-282.

Qu and Stucker."STL-based Finish Machining of Rapid Manufactured Parts and Tools." Solid Freeform Fabrication (SFF) Symposium, Austin TX, 2001, pp. 304-312.

Extract from a help file from 2004 relating to the Renishaw Productivity + system.

"How to Perfect a Machining Process (or at Least How to Make It More Trustworthy)." Modern Machine Shop, Feb. 4, 2005.

"Under Control" Modern Machine Shop, May 15, 1999.

"Key CNC Concept #4—The Forms of Compensation." Modern Machine Shop, Apr. 1, 1997.

"This Golf Ball Mold is Really Cool." Modern Machine Shop, Sep. 24, 2010.

"[IMTS Preview] AgieCharmilles to Demo Start-to-Finish Manufacturing for Mold Tooling." American Machinist, Aug. 31, 2010.

"GF AgieCharmilles and EOS Partner to Pioneer Toolmaking Process." Prototype Today, 2012.

"Process-Control The Contribution of Touch Trigger Probing." A One-Day seminar relating to Quick Change Tooling for Flexible Machining, Apr. 12, 1989, pp. 1-6.

Buckingham. "Artefact comparison techniques for achieving traceable measurement on CNC machine tools." Industrial Tooling, 1997.

Parker, Richard. "Use of Zirconia in Restorative Dentistry." Dentistry Today, Mar. 2007, pp. 114, 116, 118-119.

"NobelProcera™ Product Overview:Experience the new world of CAD/CAM dentistry." Brochure by Nobel Biocare, 2010, pp. 1-6.

"Solutions for all indications: Tooth- and implant-supported restorations for single teeth to edentulous arches." Brochure by Nobel Biocare, 2010.

"Annual Report 2009: The partner of choice in dentistry." Document by Nobel Biocare, 2009.

Olsson et al."Bridges supported by free-standing implants versus bridges supported by tooth and implant. A five-year prospective study." Pub Med, Jun. 1995.

(56) References Cited

OTHER PUBLICATIONS

Shi, Dongping. "Design based integration for improving overall quality of selective laser sintered rapid prototypes." PhD Thesis, Dec. 1999, pp. 1-147.

"Selective Laser Melting Technology Opens up New Dental and Orthopaedic Applications." 2010, EMDT (European Medical Device Technology) Website.

Kruth J. et al. "Digital manufacturing of biocompatible metal frameworks for complex dental prostheses by means of SLS/SLM." Virtual Modelling and Rapid Manufacturing, Sep. 28-Oct. 1, 2005, Portugal, pp. 139-145.

Shi et al. "Improving surface quality of selective laser sintered rapid prototype parts using robotic finishing." Proceedings of the Institution of Mechanical Engineers, Part B: Journal of Engineering Manufacture, http://pib.sagepub.com/content/214/3/197.short.

Stucker et al. "An Integrated Approach to Finish Machining of RP Parts." Solid Freeform Fabrication Symposium Proceedings, Austin TX, Aug. 2002, pp. 594-603.

http://www.cncinformation.com/rapid-prototyping-prototyping-cnc-prototype/rapid-planning-for-cnc-milling-2; Sep. 9, 2014 access date.

Video Clip from http://www.rtbot.net/play.php?id=nP1jUABA6A4 on Oct. 12, 2012. Layer Wise Metal Additive Manufacturing Video.

Video clip from http://www.dentwise.eu/dental/movies/ on Oct. 12, 2012. Dental Wise Video.

U.S. Appl. No. 14/399,754 filed under Beeby, David Nov. 7, 2014.

U.S. Appl. No. 14/399,672 filed under Beeby et al. Nov. 7, 2014.

Aug. 8, 2013 Written Opinion issued in International Patent Application No. PCT/GB2013/051208.

Jul. 9, 2013 Written Opinion issued in International Patent Application No. PCT/GB2013/051212.

Quick change Tooling for Flexible Machining.

May 24, 2018 Office Action issued in U.S. Appl. No. 14/399,754.

Jan. 9, 2018 Office Action issued in Japanese Patent Application No. 2015-510878.

Mar. 14, 2018 Office Action issued in Chinese Patent Application No. 201380036083.3.

Jul. 2, 2018 Office Action issued in Chinese Patent Application No. 201380036303.2.

Jun. 12, 2018 Final Decision of Rejection issued in Japanese Patent Application No. 2015-510879.

Jun. 12, 2018 Decision to Decline the Amendment issued in Japanese Patent Application No. 2015-510879.

Nov. 14, 2017 Office Action issued in Japanese Patent Application No. 2015-510879.

Nov. 15, 2018 Office Action issued in U.S. Appl. No. 14/399,754.

Jun. 10, 2019 Office Action Issued for U.S. Appl. No. 14/399,754.

\* cited by examiner

METHOD OF MANUFACTURING AN ARTICLE

TECHNICAL FIELD

This invention relates to a method for manufacturing an article, for example an article comprising at least one dental restoration.

BACKROUND

Rapid manufacturing techniques are becoming more widely used to produce a wide variety of parts. In particular, techniques which build parts layer-by-layer are becoming more well known and used in industry to manufacture custom parts. Selective laser sintering is one such rapid manufacturing technique whereby products can be built up from powdered material, such as powdered metal, layer-by-layer. For example, a layer of powdered material can be applied to a bed of the laser sintering machine and a laser is then controlled so as to sinter or melt select parts of the powdered material so as to form a first layer of the part. Another layer of powder is then applied on top and the laser is again controlled to sinter or melt another layer of the part. This process is repeated until the whole part is formed. The formed part is then removed from the bed of powder. Such techniques are well known and for instance described in EP1021997 and EP1464298.

Compared to more traditional techniques such as milling parts from billets or blanks, such techniques offer rapid manufacturing, as well as facilitate manufacturing of complex parts and can help to minimise material wastage. As a result it is becoming more desirable to manufacture parts using such techniques. Indeed, it is known to use such a technique for forming dental restorations, and in particular dental frameworks, which are typically complex bespoke parts.

However, products made by such a technique sometimes need a further operation in order to alter the surface finish, and/or the precision of certain features on the part, which cannot be achieved via the rapid manufacturing technique alone.

EP1974688 discloses a technique in which a plurality of dental prostheses are formed by a rapid prototyping method within a frame, with the frame being held within a finishing machine tool. WO2011/124474 discloses a grip fixture and connector structure to grip a semifinished part in a finishing machine tool, the semifinished part being formed by selective laser sintering. EP2238941 discloses a drill template formed by rapid prototyping with reference points used to position the drill template in a milling machine for subsequent processing. WO2012/064257, published after the priority date of the present application, discloses a dental bridge intermediary structure comprising a superstructure, the superstructure comprising a connection piece, the connection piece comprising connection means for connecting the dental bridge intermediary structure to a cutter.

The present application describes a method of manufacturing, via an additive manufacturing process, an article which comprises at least one (e.g. a set of) mounting feature(s) and which when subsequently mounted in a holding device of a machine tool control the position of the article to a known position and orientation.

SUMMARY

According to a first aspect of the invention there is provided a method of manufacturing an article comprising: taking an article formed in an initial state using an additive manufacturing process, the article comprising at least one (e.g. a set of) mounting feature(s); performing a second manufacturing process to transform the article into a second state, which comprises mounting, via the at least one (e.g. set of) mounting feature(s), the article in a holding device of a machine for operating on the article, wherein the position and orientation of the article, for example in three linear and three rotational degrees of freedom, within the machine operating volume is constrained by (and for example is known and defined by) virtue of the interaction of the at least one (e.g. set of) mounting feature(s) with the holding device, and processing at least one feature on the article.

Accordingly, the additive manufacturing process could have been used to form the bulk of the article and the second manufacturing process could be used to finish off certain aspects or features of the article. The provision of at least one mounting feature(s) which defines the position of the article within the machine operating volume can obviate the need to probe the article to determine its location prior to operating on the article. The at least one mounting feature(s) can ensure that the position and orientation of the article is known when it is mounted in the machine. In particular, it can ensure that the lateral position in three orthogonal degrees of freedom, and the rotational orientation about three orthogonal rotation axes is constrained in a known way. Accordingly, the at least one mounting feature(s) could be described as being a location defining mounting feature. This can mean that the processing of the at least one feature on the article can take place straight away without time consuming position and/or orientation identification operations which require inspection of the location of the article, e.g. without probing the article to find its location.

There can be two main sources of error in the position of the at least one feature to be processed. One source of error can be the uncertainty in the position of the at least one feature to be machined relative to the at least one (e.g. set of) mounting feature(s) (and hence relative to the holding device of the machine). This error can be dependent on the accuracy of the additive manufacturing process. Accordingly, such errors can vary depending on the accuracy of the additive manufacturing process, but typically are known and can be defined with respect to the process used. Another source of error can be the position repeatability of the article with the holding device of the machine (which can be dictated by the configuration of the at least one (e.g. set of) mounting feature(s) and corresponding features on the holding device). Preferably, the at least one (e.g. set of) mounting feature(s) are configured such that the ratio of i) uncertainty of the position of the part (e.g. at least one feature to be machined) to ii) the position repeatability of the article is not more than 50:1, more preferably not more than 10:1, especially preferably not more than 5:1, for example not more than 4:1, for instance not more than 1:2. As will be understood, the uncertainty of the position of the part and the position repeatability of the article can be measured as position tolerance diameters.

Accordingly, preferably the method is configured, and for example the at least one (e.g. set of) mounting feature(s) of the article and the holding device are configured, such that when the article is mounted in the holding device, the location of the at least one feature to be processed within the machine's operating volume is known to within a required, e.g. predetermined, tolerance, and for example to within a position tolerance diameter of 100 μm (microns), more preferably to within a position tolerance diameter of 50 μm (microns).

The at least one (e.g. set of) mounting feature(s) could be configured such that the linear position along all three mutually perpendicular axes and rotational orientation about those axes within the machine operating volume is known and defined by virtue of the interaction of the at least one (e.g. set of) mounting feature(s) with the holding device.

For example, the at least one (e.g. set of) mounting feature(s) can be kinematic mounting features. As will be understood, and as for instance described in H. J. J. Braddick, "Mechanical Design of Laboratory Apparatus", Chapman & Hall, London, 1960, pages 11-30, kinematic design involves constraining the degrees of freedom of motion of a body or feature using the minimum number of constraints and in particular involves avoiding over constraining. This ensures highly repeatable positioning of the article with respect to the holding device, and means that the article will sit on the holding device in a predictable known manner. Accordingly, such kinematic mount features could engage with corresponding kinematic mount features on the holding device of the tool (e.g. machine tool) for operating on the article.

It has not previously been considered to use kinematic mount features to hold an article for machining due to the high loads experienced during machining. There has therefore been a technical prejudice against the use of kinematic mount features for this purpose.

The article can also comprise gross orientation features which restrict the gross orientation that the user can place the article on the holding device. In particular, preferably they are configured such that they enable the article to be placed in one orientation only on the holding device. Such feature could be provided by the at least one (e.g. set of) mounting feature(s). Optionally, they are provided as separate features to the at least one (e.g. set of) mounting feature(s). Preferably, such gross orientation features do not interfere with the control of the position and orientation of the article provided by the engagement of the at least one (e.g. set of) mounting feature(s) on the article and corresponding features on the holding device.

The article could have been built via the additive manufacturing process according to a computer model e.g. a CAD model, of the article.

Accordingly, the second manufacturing process could comprise determining the location of features of the article using data concerning the position of such features. Such data could be derived from the computer model Accordingly, the method can comprise receiving data concerning the position of at least some features of the article.

The article could have been built layer-by-layer via the additive manufacturing process. The article could have been built via a laser consolidation processes, such as a laser sintering or melting process, also known as selective laser sintering or selective laser melting. Optionally, the article could have been built via a laser cladding process, a fused deposition modelling (FDM) process or an e-beam melting process. The method can comprise the step of forming the article via the additive process.

The second manufacturing process can be a subtractive process. Accordingly, processing the at least one first feature can comprise removing material from the article. For example the machine can be a machine tool, and in which the second manufacturing process comprises machining, for example milling, at least a part of the article.

The article could be processed from multiple sides. For instance, the article could be processed on opposing sides. This could be achieved by mounting the article such that it can be accessed on multiple sides by the processing machine. This could be achieved by turning the article during the second manufacturing process. Accordingly, the second manufacturing process can comprise processing a first side of the article and subsequently turning the article so as to perform an operation on another side of the article. More particularly, the second manufacturing process can comprise processing a first side of the article and subsequently turning the article over so as to perform an operation on an opposite side of the article. This could for example comprise machining a first side of the article and subsequently turning the article so as to machine an opposite side of the article. The article could be turned by the holding device. That is the holding device could have an axis of rotation.

It might be that the at least one first feature is formed entirely during the second manufacturing process. Optionally, the at least one first feature can have already been at least partially formed in the article via the additive manufacturing process. Accordingly, processing the at least one first feature can comprise finishing the at least one first feature. This could comprise removing material on the at least one first feature. Accordingly, the at least one first feature could be provided with excess material which is removed during the second manufacturing process. Accordingly, when the method comprises forming the article via the additive processes, this step can comprise adding excess material onto at least the at least one first feature. Such excess material can be material in excess to what is ultimately desired for the finished product.

The article can comprise at least one dental restoration. The article could comprise at least one implant supported dental restoration. The dental restoration could be an abutment. The dental restoration could be a single tooth restoration, for example an implant supported abutment or a crown. Other material could be added to the dental restoration to finish the restoration. For instance, porcelain or a crown could be added to provide a finish that is more aesthetically similar to natural teeth.

The second manufacturing process can comprise machining a part of the dental restoration that is to interface with another object, e.g. another member in a patient's mouth. This can be important to ensure a good fit. Ensuring a good fit can be important for many reasons, e.g. structurally so as to reduce the chance of failure of the dental restoration. It can also be important to ensure a good fit so as to reduce or avoid gaps which could harbour bacteria. For instance, the method can comprise machining a region that is to interface with a tooth prepared for receiving the restoration, commonly known as a "prep" in a patient's mouth, or an implant in a patient's jaw. The dental restoration could comprise at least one portion for interfacing with at least one member in a patient's mouth, e.g. at least one implant member, and the second manufacturing process comprises machining said at least one portion.

The article can comprise a plurality of products joined together. As will be understood, the products can be subsequently separated from each other. Accordingly, a plurality of products can be formed and processed concurrently. As they are joined together, they can be transported together and mounted together in a machine for performing the second manufacturing process.

The article can comprise at least one product and at least one member on which the at least one (e.g. set of) mounting feature(s) are provided. Accordingly, the at least one (e.g. set of) mounting feature(s) can be provided separate from the product(s). As will be understood, the at least one member can be subsequently separated from the product subsequent to all processing requiring the member. The member could be a holding member (e.g. a clamp member) via which the article can be held (e.g. clamped) to define and maintain its location during the second manufacturing process. The at least one member may comprise a central hub around which the at least one product is arranged.

The plurality of products can be joined together via the at least one member.

The plurality of products can comprise a plurality of dental restorations. For instance, the plurality of products can comprise a plurality of dental abutments.

Where the article was been supported during the additive manufacturing process by scaffolding on a lower side of the article, the at least one feature being processed on the article may be on the same side as said scaffolding.

The at least one feature may be processed on the article during the second manufacturing process on a surface of the article on which the scaffolding was provided.

According to another aspect of the invention, there is provided a method of manufacturing an article comprising: taking an article in an initial state formed using an additive manufacturing process, the article comprising at least one mounting feature; and performing a second manufacturing process to transform the article into a second state, which comprises mounting, via the at least one mounting feature, the article in a holding device of a machine for operating on the article, and processing at least one feature on the article; wherein the article was supported during the additive manufacturing process by scaffolding on a lower side of the article, and wherein the at least one feature is processed on the article during the second manufacturing process on the same side as said scaffolding.

The position and orientation of the article in three linear and three rotational degrees of freedom within the machine operating volume may be known and defined by virtue of the interaction of the at least one mounting feature with the holding device.

The at least one mounting feature may comprise kinematic mount features which engage with corresponding kinematic mount features on the holding device of the machine tool.

The at least one feature may be processed on the article during the second manufacturing process on a surface of the article on which the scaffolding was provided.

According to another aspect of the invention, there is provided a method of manufacturing a dental restoration comprising: i) forming a dental restoration body in an initial state via an additive process, the dental restoration body comprising a mount having at least one set of location features; ii) mounting the dental restoration body in its initial state into a machine tool via the mount's at least one set of location features; and iii) machining the dental restoration body from both substantially opposing first and second sides of the dental restoration body to transform the dental restoration body into a secondary state.

Accordingly, the method of the invention utilises different manufacturing techniques at different stages to form an accurate dental restoration in an efficient manner.

The use of an additive process can be advantageous over machining the entire dental restoration body from a solid blank as it requires significantly less material and also can be less time consuming. It also allows the formation of a geometry that would be impossible with machining processes alone.

The provision of the location features can remove the need for probing to ascertain the dental restoration body's position within the machine tool. The location features can ensure that the location of the dental restoration body is known when it is mounted in the machine tool.

Step iii) can comprise machining the dental restoration body from the first side of the dental restoration body, re-orienting the initial state dental restoration, and then machining the dental restoration body from the second side of the initial state dental restoration body.

The at least one set of location features can comprise at least one set of kinematic mounting features.

The dental restoration body can comprise at least one interface for interfacing with an implant in a patient's jaw (so as to locate the dental restoration in the patent's jaw) which is presented on one of said first and second sides of the dental restoration.

It can be important that the at least one interface (the area(s) of the dental restoration body which mate with the implant(s) in the patient's jaw) has a very precise finish. Without such a precise finish, the fit between the implant(s) and interface(s) could be inadequate and which can lead to the dental restoration being inadequately secured within the patient's jaw.

Accordingly, in the dental restoration body's initial state, the at least one interface can be formed with an excess of required material. The method can further comprise machining said at least one interface to remove at least some of said excess material.

A plurality of interfaces, spaced along the dental restoration body can be provided. This is especially the case when the dental restoration is an implant bridge. It has been found that if the plurality of interfaces are not accurately formed, for example if the spacing between the interfaces differs from the spacing between the corresponding implants in the patient's jaw, then the dental restoration body can become contorted when fixed into position. This contortion can leads to stresses in the dental restoration body, which in turn can lead to undesired stresses on the implants. Such stress on the mounts can cause discomfort for the wearer and a tendency for the dental restoration body to work itself loose, or even fail.

Accordingly, the method can comprise machining at least one of said plurality of interfaces so as to remove excess material, thereby manipulating the relative position of said plurality of interfaces relative to each other.

The at least one interface can be provided on the second side of the dental restoration body.

The at least one interface can be an implant interface for interfacing with an implant secured into a patient's jaw.

The dental restoration body in its initial state can comprise at least one bore for receiving a fastener for securing the dental restoration body to an implant in a patient's jaw. As will be understood, the surface against which the head of a fastener abuts the dental restoration body against can require a high level of smoothness in order to ensure a secure fit. The method can therefore comprise machining said at least one bore so as to provide a final formation of said at least one bore.

The machining of said at least one bore can be performed from said first side of the dental restoration body.

An additive process can comprise a selective laser melting/sintering process.

The dental restoration can be an abutment. The dental restoration can be an implant supported abutment.

The dental restoration body can form the final outer shape of the dental restoration. Optionally, the dental restoration body can be a body, or "framework", onto which an outer structure can be formed to provide the final outer shape of the dental restoration. Accordingly, the method can comprise adding an outer structure onto the body. The outer structure can comprise a layer of porcelain.

According to another aspect of the invention there is provided a method of manufacturing an article comprising: forming an article in an initial state using an additive manufacturing process, the article comprising at least one (e.g. set of) mounting feature(s), e.g. at least one set of kinematic mount features (i.e. formed via the additive manufacturing process). The method can comprise mounting the article in a holding device of a machine via the set of kinematic mount features.

According to a further aspect of the invention there is provided an article made by an additive manufacturing process comprising at least one (e.g. set of) mounting feature(s), e.g. at least one set of kinematic mount features.

According to a further aspect of the invention there is provided an article made by an additive manufacturing process comprising at least one feature requiring processing in a second manufacturing process, wherein the article was supported during the additive manufacturing process by scaffolding on a lower side of the article, and wherein the at least one feature to be processed during the second manufacturing process is on the same side as said scaffolding. The scaffolding, or at least remnants thereof, may remain on the article.

The article may comprise at least one dental restoration.

The at least one feature may comprise at least one portion of the dental restoration that is to interface with another member in a patient's mouth. The second manufacturing process may be one in which said at least one portion is machined.

The at least one feature may comprise at least one portion for interfacing with at least one implant member.

According to a further aspect of the invention there is provided a method of manufacturing an article comprising: taking an article in an initial state, the article comprising at least one mounting feature; and performing a series of two or more manufacturing processes to transform the article into a different respective state in each manufacturing process of the series, comprising, for each manufacturing process of the series: mounting, via the at least one mounting feature, the article in a holding device of a machine for operating on the article during that manufacturing process, wherein the position and orientation of the article in three linear and three rotational degrees of freedom within the machine operating volume is known and defined by virtue of the interaction of the at least one mounting feature with the holding device, and processing the article.

The at least one mounting feature may comprise kinematic mount features which engage with corresponding kinematic mount features on the holding device of the machine.

The article in the initial state, with the at least one mounting feature, may be formed using an additive manufacturing process.

According to a further aspect of the invention there is provided a product or article produced by a method as described herein.

This application also describes a method of manufacturing a dental implant-supported abutment comprising: building an abutment, including the part for interfacing with an implant member, from a powdered material, layer-by-layer, via a laser sintering process. Such a method can comprise processing at least a part of the abutment subsequent to said laser sintering process.

Said processing can comprise removing material from the abutment, e.g. via machining. The method can comprise processing the part for interfacing with an implant member. Processing can comprise, subsequent to said laser sintering process, mounting the abutment in a device for holding the abutment during said processing. The laser sintering process can comprise building a mount connected to the abutment via which the abutment is mounted in the device for holding the abutment during said processing. Preferably, the abutment and mount are configured such that when the abutment is mounted in the device for holding the abutment during said processing, the abutment's longitudinal axis, which could for example be parallel or even coincident with the axis of any current or yet to be formed bore of the abutment (through which an implant screw, or screwdriver for fastening an implant screw can be received), and optionally for example the axis of the part for interfacing with the implant member, is parallel to the tool, e.g. cutting tool, for processing the abutment. The laser sintering process can comprise building a plurality of abutments connected to the same mount. At least two, and preferably all, of the plurality of abutments can be oriented such that their part for interfacing with an implant member are oriented in the same direction, e.g. such that their longitudinal axes are parallel to each other.

DETAILED DESCRIPTION

The below description provides an example of how the invention can be used to manufacture an implant-supported abutment. As will be understood, an implant-supported abutment is a particular type of dental restoration which in use is secured to a dental implant already implanted into a patient's jaw so as to retain the dental restoration in the patient's mouth. Typically, an implant-supported abutment is used to replace a single tooth. Implant-supported abutments are typically made from a base structure of metal, with porcelain, a bridge or a crown being added to the abutment before it is fitted to provide the desired finish form and look of the abutment.

As will be understood, the invention is not limited to the manufacture of implant-supported abutments, but could also be used for instance in the manufacture of other types of dental restorations, such as bridges or crowns. However, the invention is also not limited to dental restorations in general. Rather, the invention can be used in the manufacture of a wide range of different types of products, such as other types of medical implants, aerospace parts and jewellery.

As will be understood, an implant supported abutment needs to be made accurately so as to ensure that the abutment provides a comfortable and enduring fit in a patient's mouth. It is known to use a machine tool, such as a CNC milling machine to produce a dental abutment from a blank or "billet" of sufficient volume so that the entire abutment can be machined in one piece. As will be understood, for implant-supported abutments, the blank can be a solid piece of metal, for example titanium or a cobalt chrome alloy. Other materials can be used, for instance zirconia, although in this case, a metal link member is sometimes required between the zirconia body and implant. In any case, such a milling/machining technique results in a highly accurate abutment being formed, but is time consuming, expensive and involves significant material wastage The embodiment described according to the present invention makes use of an additive process to produce an initial form of the abutment. An additional machining process is then used to further process at least a select region of the abutment. The use of an additive process can be advantageous over machining the entire dental restoration body from a solid blank as it requires significantly less material and also can be less time consuming.

Figure 1:
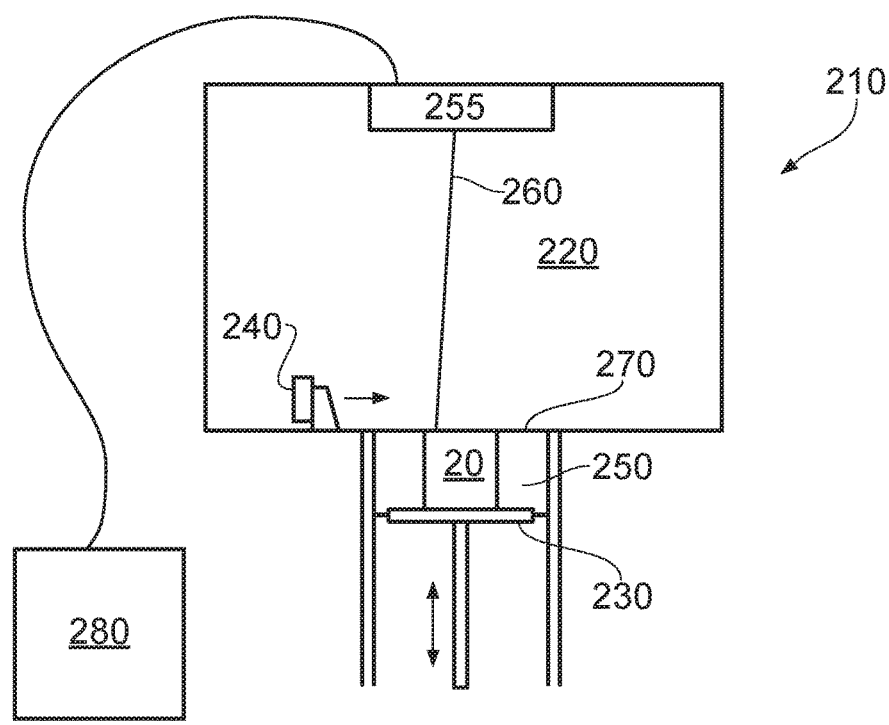
FIG. 1 shows schematically a selective laser sintering machine for forming an article.

FIG. 1 illustrates a typical arrangement of a build chamber 210 of a selective laser sintering/melting machine. The build chamber 210 defines a space 220 above a lowerable build platform 230. The build chamber 210 comprises a powder dispensing and coating apparatus 240 for spreading powder 250 over the surface of the build platform 230. A window 255 in an upper wall of the chamber 210 allows a laser beam 260 to be directed to irradiate powder spread at a build surface 270, so as to selectively sinter/melt the powder thereby forming a layer of the article 20 to be manufactured. The laser and lowerable platform 230 can be controlled by a controller, 280, such as a PC, which has a program defining the process for forming the article 20. The program can control the laser sintering process on the basis of CAD data of the part to be formed. In particular, the CAD data can be split into a number of layers, each layer corresponding to a layer to be formed by the laser sintering process.

Figure 2:
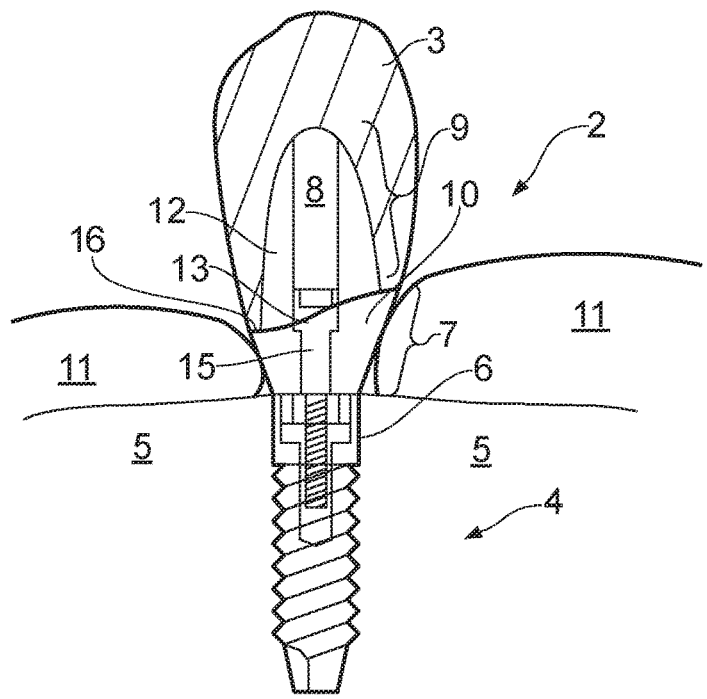
FIG. 2 shows schematically a cross-sectional view of an implant abutment attached to a supporting implant.
Figure 3A:
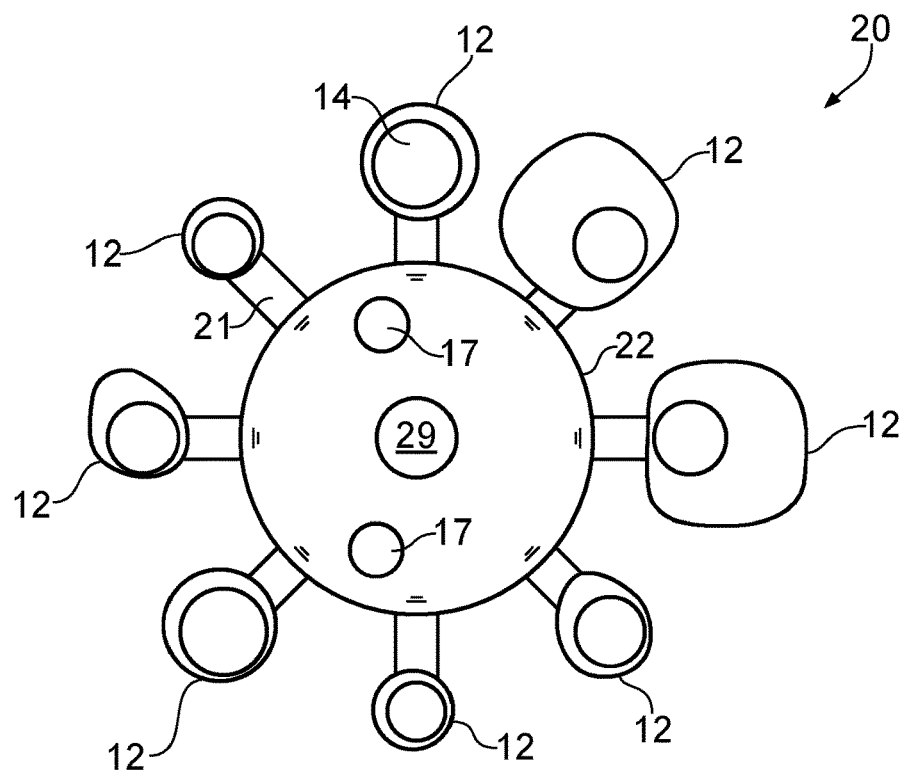
FIGS. 3a and 3b show schematically underside views of an article comprising a plurality of abutments connected to a central hub in its initial state.
Figure 3B:
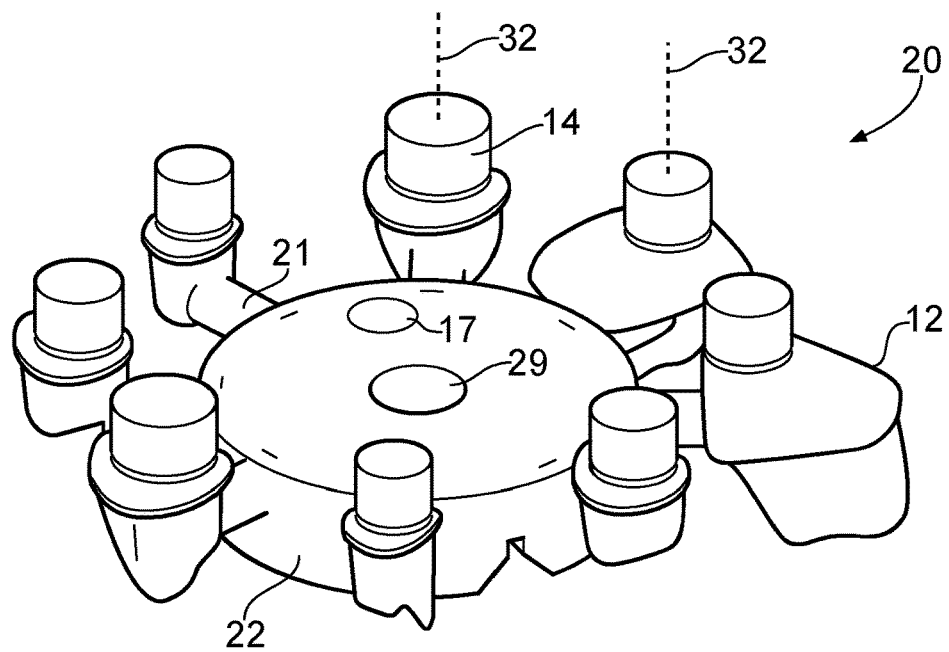
Figure 4A:
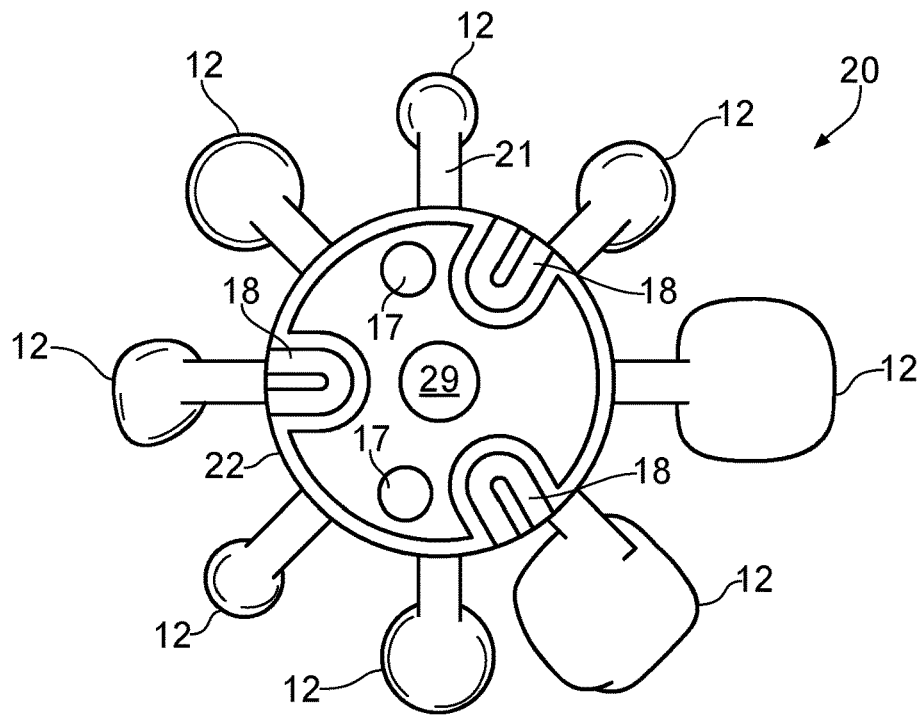
FIGS. 4a and 4b show schematically top-side views of the article shown in FIG. 3.
Figure 4B:
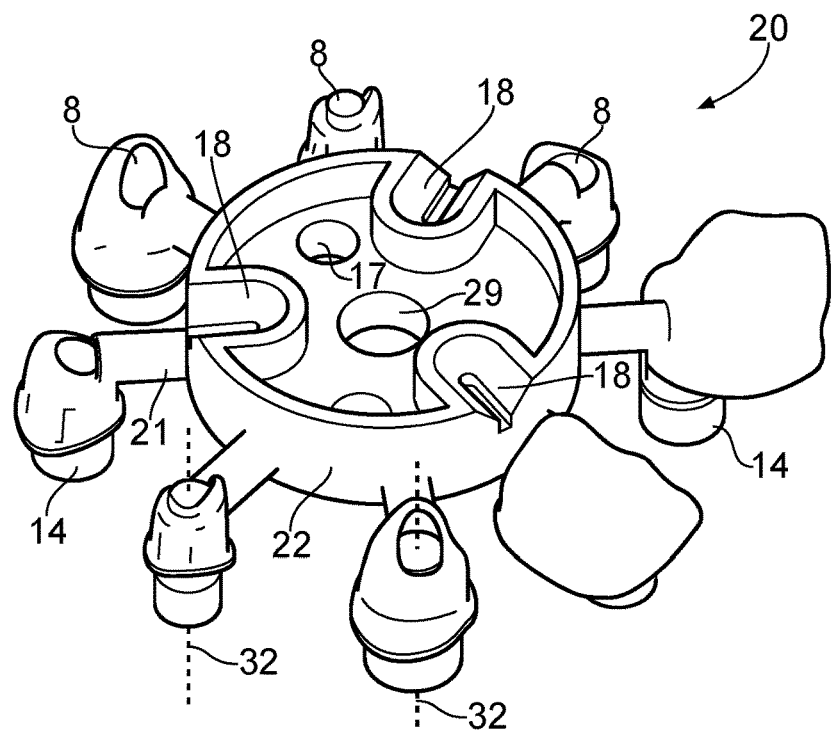

FIG. 2 illustrates how a completed dental restoration, in this case an implant abutment 12, in its final state may be affixed to an implant 4 in a patient's jaw bone 5. Neighbouring teeth are not shown in this drawing for sake of simplicity. As shown, an outer layer of porcelain 3 is added to the abutment 12 to provide the final outer shape of the dental restoration 2. FIG. 2 shows the implant/abutment interface 6, which is the region at which the abutment 12 and the implant 4 engage each other. This is a portion of the abutment's 12 surface that is to be finished to a high degree of accuracy. As shown, the abutment 12 comprises a counter bore 8 formed in it into which an implant screw 10 can be located. The counter bore 8 comprises an upper section 13 and lower section 15. The lower section 15 has a smaller radius than the upper section 13, and in particular has a radius smaller than the head of the screw 10 which is used to secure the abutment 12 to the implant 4. As shown, when screwed into the implant 4 through the counter bore 8, the screw 10 securely fastens the counter bore 8, and hence the abutment 12, to the implant 4.

Also shown in FIG. 2 is the emergence profile region 7 between i) the implant interface 6 and ii) the portion 9 of the abutment 12 onto which the porcelain/crown is added (often referred to as the coronal region 9). This emergence profile region can also be described as being the region between the implant interface 6 and the abutment's margin line 16. As will be understood the margin line is commonly understood as being the edge around the abutment up to which the porcelain or crown is intended to be provided. This region of the abutment's metal surface is therefore exposed and in direct contact with the patient's gums 11, or gingiva. This region is commonly referred to in the dental field as the "emergence profile", or the "transgingival region". It can be important that this emergence profile region 7 is smooth so as to avoid irritation or the gingiva and also to prevent the harbouring of bacteria. This area can be smoothed via appropriate polishing techniques.

Figure 8A:
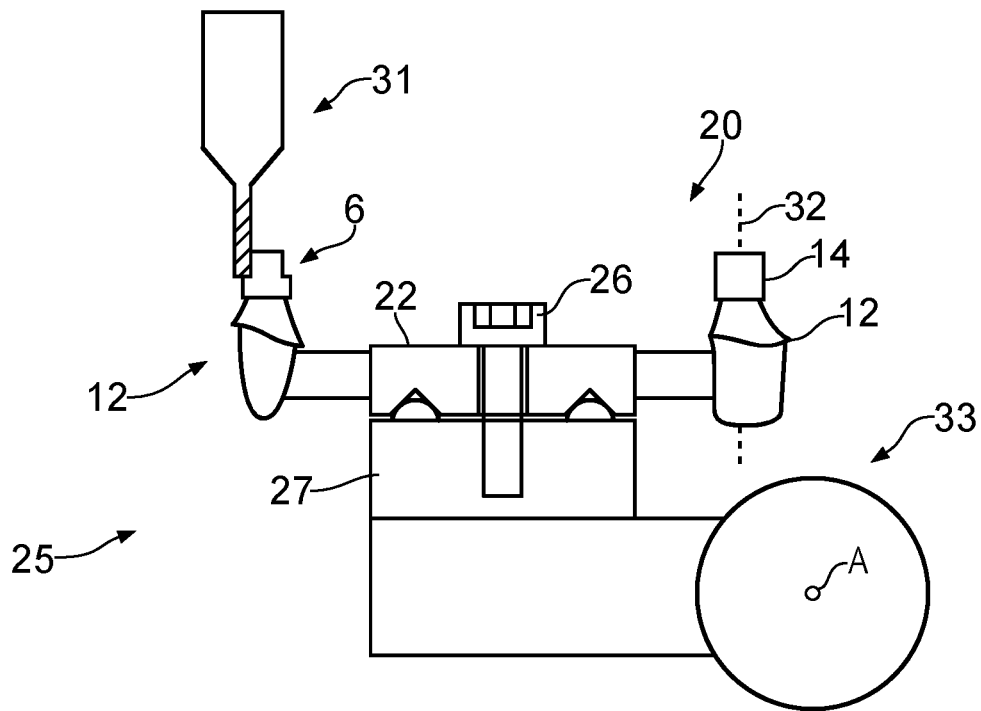
FIG. 8a shows schematically the implant interfaces being machined into the underside of a dental restoration and FIG. 8b shows schematically the article turned upside down by the clamp member in preparation for counter bores to be machined into the abutments.

FIGS. 3a and 3b, and FIGS. 4a and 4b respectively show underside and top-side views of an article 20 made from powdered cobalt-chrome via a laser sintering process which comprises a plurality of individual abutments 12 each of which is attached to a common location hub 22 via a connecting bar 21. As shown, the lowermost surface of each abutment 12 comprises a circular disk/boss-like protrusion of excess material 14 from which the abutment's 12 implant interface 6 is still to be formed via machining. The figures also show that on one side of the location hub 22, there are provided three v-groove features 18 defining a kinematic mount. As described below, the three v-groove features 18 are used to accurately locate the article 20 in a known position and orientation in the machine tool apparatus' volume via the machine tool clamp 25 (described in more detail below). As also shown, the location hub 22 also comprise two gross-orientation bores 17 extending all the way though the location hub 22. As described below, these bores 17 can be used to ensure the correct gross orientation of the article 20 in the machine tool clamp 25. As shown, all of the abutments 12 are oriented such that their longitudinal axes 32 are parallel to each other. Furthermore (and as illustrated in FIG. 8a) the abutment and mount are configured such that when the article 20 is mounted in the clamp 25 during subsequent processing, the abutment's longitudinal axis 32, is parallel to the cutting tool's 31 longitudinal axis.

Figure 5:
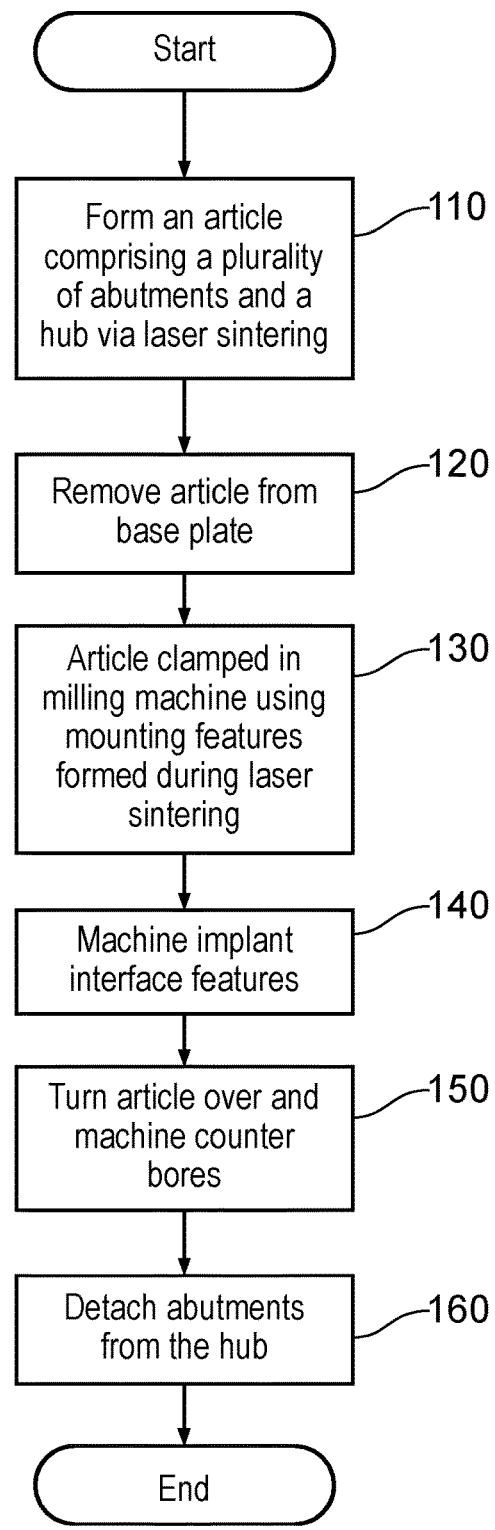
FIG. 5 is a flowchart illustrating a method according to the invention.

FIG. 5 is a flowchart illustrating the method of producing an implant-supported abutment 12 according to one embodiment of the invention. Each of the steps illustrated will be explained with reference to FIGS. 6 to 8.

In the first step 110, the abutment 12 in its initial state is produced using a rapid manufacturing process, which in this example is a selective laser sintering process. As will be understood, the selective laser sintering process comprises using a selective laser sintering machine such as that schematically shown in FIG. 1 and described above, to repeatedly add layers of powdered material to the article 20. A high intensity laser is focussed on the region of the powdered material corresponding to the appropriate shape of the article 20 for the appropriate layer, so as to bind the powder. Subsequently, the surface on which the sintering takes place is lowered, so that when the powdered material is next applied the laser may focus at the same height, but scanned around an appropriate course across the powder. In the embodiment described, the abutment 12 is formed as part of an article 20 that comprises a plurality of abutments 12 (in this example eight abutments) which are connected to a hub 22 also formed by the laser sintering process.

Figure 6:
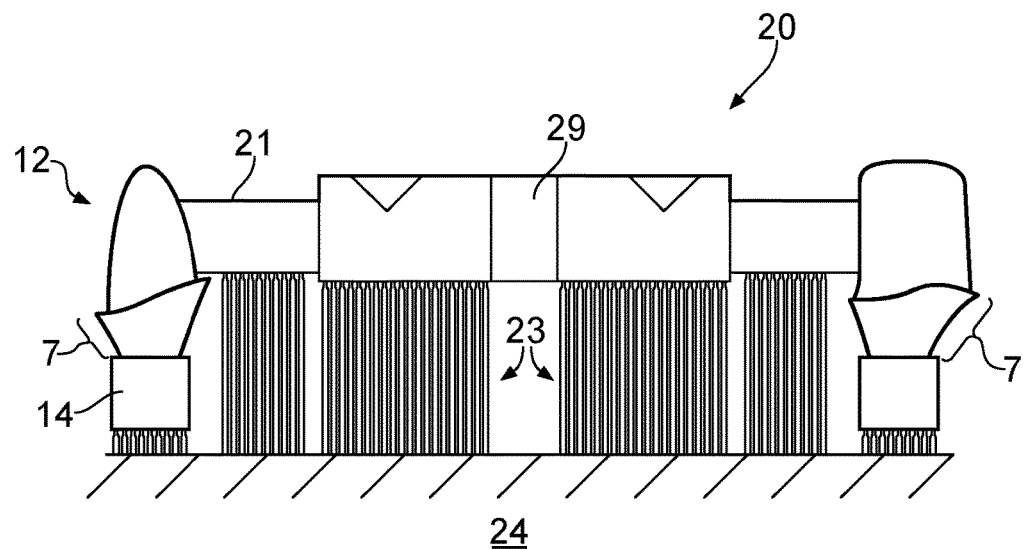
FIG. 6 shows schematically a cross-sectional side view of the laser sintered article of FIGS. 3 and 4 still attached to a build plate during manufacture.

FIG. 6 shows a cross-section view of an article 20 having been constructed by selective laser sintering, but still located on a build plate 24. The article 20 is resting on a support structure 23, which is a web of sintered material of lesser density than the article, but is of sufficient strength to support the article and to prevent both distortion under its own weight and internal thermal stresses; the support structure 23 is also referred to herein as scaffolding or a support web. As will be understood, although not shown, the build plate 24 may be considerably larger than the article 20 being produced and as such may permit several articles to be built simultaneously. It can also be seen from FIG. 6 that, where the article 20 is supported during the additive manufacturing process by scaffolding 23 on a lower side of the article 20, the mounting feature(s) 18 is/are provided on a different side of the article 20, free from the scaffolding 23 (i.e. on an upper side of the article 20).

The second step 120 follows the completion of the selective laser sintering process, and comprises removing the build plate 24 and the article 20 from the selective laser sintering apparatus and preparing them for machining. Preparation can include various optional stages such as placing the article 20, along with support web 23 and build plate 24 into an industrial oven, in order that a stress relief heat treatment cycle may be conducted. The article 20 is then removed from the build plate 24 by cutting the support structures 23, with any remaining parts of the structure 23 removed by pliers and abrasive rotary tools. The article 20 can then be grit blasted to make the entire surface smoother. Even after grit blasting, the side of the article 20 that was connected to the support structure 23 can sometimes (depending for example on the use of abrasive tools before blasting) still be significantly rougher than the opposite side, due to remnants of the support structure 23 remaining on the article 20. As shown, the abutments' 12 emergence profile regions 7 and the excess material 14 from which the implant interfaces are to be machined are found on the surface of the article 20 on which the support structure 23 was provided.

As previously stated, the machining of the abutments 12 in its initial state can be a multiple stage process, as the abutment 12 can require features to be machined from inverse orientations.

Figure 7:
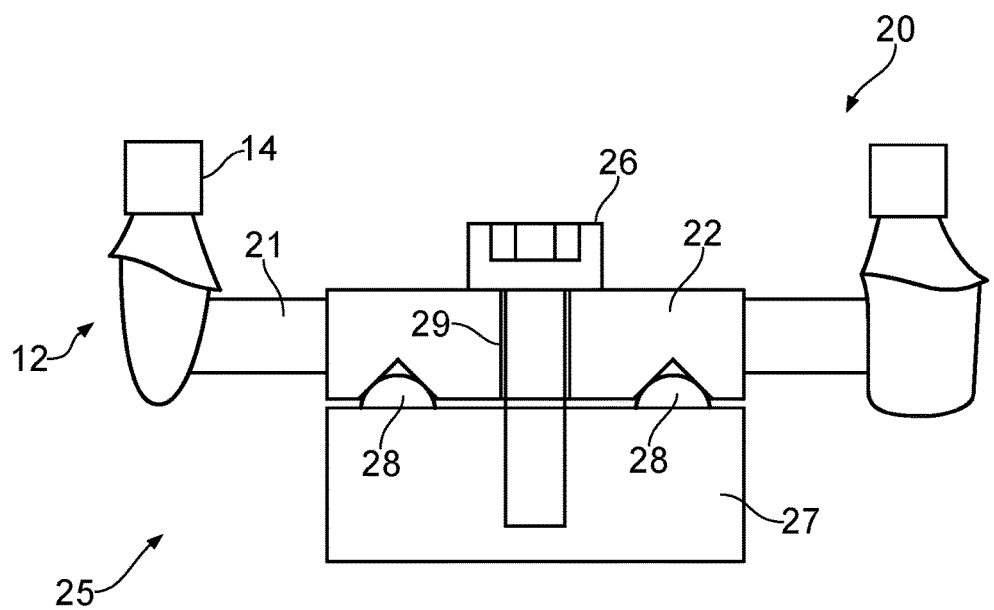
FIG. 7 shows a schematic cross-sectional side view of the laser sintered article of FIGS. 3 and 4 clamped using a kinematic mount in a machine tool.

As illustrated by FIG. 7, the following step 130 comprises mounting the article in its initial state onto a mounting structure, in this case clamp 25, in the machine tool, for example a computer numerically controlled (CNC) milling machine. FIG. 7 shows schematically a view of the article 20 in its initial state clamped into position by the clamp 25 engaging the location hub 22. The clamp 25 comprises a base 27 having three hemispherical protrusions 28 (only two of which are shown in FIG. 7) located on its upper surface 30. The protrusions 28 are arranged such that they can engage with the kinematic features 18 on the location hub 22, thereby facilitating kinematic mounting of the article 20 onto the clamp 25. The clamp 25 also comprises an upper clamping member 26 which engages the location hub 22 so as to urge the location hub 22 into the base 27, thereby securely holding the article 20 in place. In this case, the upper clamping member is a screw 26 that extends through a hole 29 in the location hub 22 so that its screw thread (not shown) engages with a cooperating screw thread in the base member 27, and such that as it is tightened, the head of the screw 26 pushes the kinematic features 18 of the location hub 22 into kinematic features 28 of the base 27. The article 20 is clamped such that the surface to be machined is facing upwards.

Then at step 140, and as illustrated by FIG. 8a, the excess material 14 provided on each abutment 12 is machined by a milling tool 31 of a computer numerically controlled (CNC) machine tool apparatus so as to form an implant interface structure 6 which can engage with corresponding features on an implant 4. The kinematic features constrain the position and orientation of article 20 and hence the abutments 12 within the machine tool's operating volume in all three linear and all three rotational degrees of freedom. Accordingly, this machining step can take place without the requirement to probe the article 20 to determine its location. That is, the position of the abutments 12 can be assumed from knowledge of where they should be with respect to the location hub 22. In the present example, each article 20 is made according to a standard model such that each excess material portion 14 can be assumed to be in a predefined position. That is, it is known that the article 20 will comprise eight abutments 12 and that the excess material portion 14 of each abutment 12 will be in a predefined location with respect to the location hub 22. In particular, in this embodiment the method, and in particular the kinematic features, are configured such that the position of the abutments 12, and more particularly the position of the excess material portions 14, are known within a position tolerance diameter of 100 μm (microns). Accordingly, the accuracy of the laser sintering process is such that the uncertainty of the position of each abutment 12 relative to the kinematic mounting features 18 is within a position tolerance diameter of 80 μm (microns) and the position repeatability of the assembly is within a position tolerance diameter of 8 μm (microns). Hence the ratio of i) the uncertainty of the position of each abutment 12 relative to the kinematic mounting features to ii) the repeatability of the kinematic mount features is 10:1.

As the location of the location hub 22 is accurately defined by the kinematic mounting features 18 and 28 on the hub 22 and base 27, the position of the excess material portions is also accurately defined and known and can be assumed by the machine tool apparatus performing the milling operation. As will be understood, this need not necessarily be the case and for instance the location of certain features, such as the excess material portions 14, can be determined from data indicating the position of the features, for instance as determined from, for example, a CAD model of the article used to produce the article during the laser sintering step.

Figure 8B:
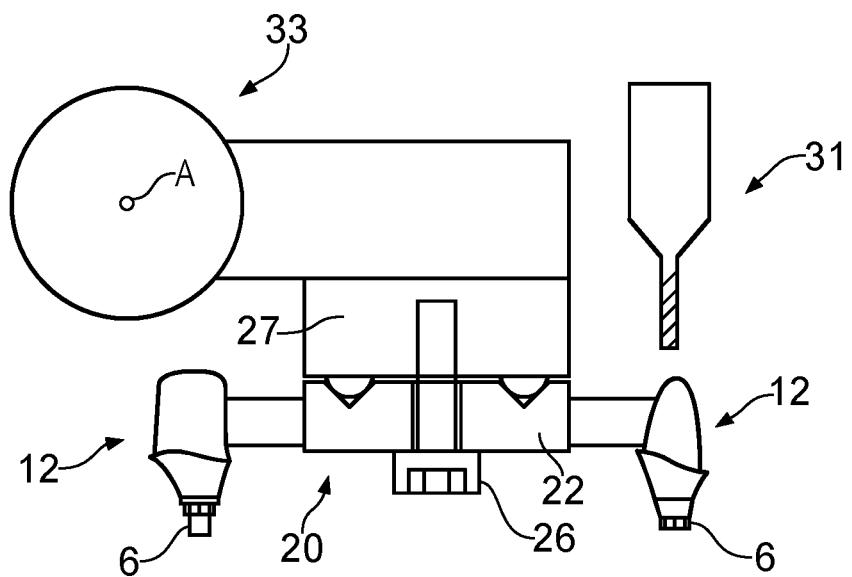

In the embodiment described, the clamp's base 27 is connected to a rotation unit 33 which enables the clamp 25 to be rotated about a rotational axis A, such that the article 20 can be turned upside down in the machine tool apparatus. A calibration routine has already been performed such that it is known how rotation of the clamp 25 about the axis A affects the position of the article 20. Accordingly, the next step 150 involves turning the article 20 over as illustrated by FIG. 8b and then machining the counter bores 8 so as to finish them to ensure an intimate contact between screw head's shoulder and the mating surface in the counter bore 8. As the clamp 25 has already been calibrated, it is possible to accurately finish/form the bores 8 with respect to the implant interface structures 6. This is important in order to ensure alignment of the counter bores with the implant so as to avoid excess bending forces on the screw connecting the abutment to the implants. In the described embodiment, the counter bores 8 are partly formed during the additive manufacturing process and then precision finished during this machining step. However, as will be understood, this need not necessarily be the case and for example the counter bores could be entirely formed via this machining step (i.e. no counter bore structure is initially formed via the additive manufacturing step at all).

The final step 160 comprises removing the article 20 from the machine tool. The location hub 22 and connectors 21 are detached from the abutments 12, and any remains of the connectors 21 are manually ground down. A layer of porcelain 3, or a crown structure, can then be added to the abutments 12 to form the implant abutment before it is secured to the implant 4 in the patient's jaw.

An embodiment of the present invention is particularly useful for multi-stage processing of an article 20, where the article 20 is required to be processed in multiple different machines at different respective times, and is required to be held within each machine such that the position of parts of the article 20 are known. The provision of at least one mounting feature on the article 20 which defines the position of the article 20 within the machine operating volume (within the respective operating volume of each different machine in the multi-stage processing) can obviate the need to probe the article 20 at each stage to determine its location prior to operating on the article 20. The at least one mounting feature can ensure that the position and orientation of the article 20 is known when it is mounted in each machine of the multi-stage processing. It will be appreciated that such a benefit can be achieved regardless of how the at least one mounting feature is formed, i.e. it need not be by way of an additive manufacturing process but could for example be formed by a subtractive process such as milling or a combination of these. For example, the different processing stages could include an inspection stage, one or more machining stages, and a polishing stage, and one or more further machining stages. For an example of a polishing stage, WO 2013/167905. Although in WO 2013/167905 the article is not required to be held in a precise position and orientation within the electropolishing machine, and is not therefore provided with a location-defining mounting feature, it will readily be appreciated that the electropolishing machine of WO 2013/167905 can be easily adapted to receive an article having such a location-defining mounting feature. WO 2013/167905 also discloses a machining stage following the electropolishing stage, in which the article is clamped into a machine tool and in which machining operations are performed on the article, for example machining/milling of abutments.

Referring again to FIG. 6, it is noted again that the excess material 14 from which the implant interfaces are to be machined are found on the surface of the article 20 on which the support structure 23 was provided, i.e. on the same side as the support structure 23. This is somewhat counter-intuitive, because normally one would arrange the article 20 during the additive build process in such a way as to place the support structure 23 away from those surfaces that are considered to be critical, and to place them on surfaces that do not require a smooth or accurate finish.

For example, for dental frameworks, the critical parts are the implant interfaces, and the upper surface of the framework is less critical because that will anyway be covered by a layer of porcelain; it is the porcelain that will give the dental restoration its final appearance. In fact, any surface roughness caused by remnants of the support structure 23 remaining on the article 20 could be considered as advantageous, for acting as a key for holding the porcelain layer securely.

However, the present applicant has appreciated that there are significant benefits in some applications of doing the opposite of what is considered to be normal, that is to arrange the support structure 23 on the same side as the critical interfaces, or any other feature that is being processed in the second manufacturing stage. In a two-stage manufacturing process in which the critical interfaces are being machined anyway in the second stage, the presence of the support structure on the critical interfaces is not an issue. Performing the additive manufacturing in this orientation also means that there is no manual finishing or grinding required on the top surface (for example of an implant bridge); in this respect it is often required to attach a pre-made article to this top surface and if it had supports on the surface, which are ground away, it is unlikely that the surface will have retained sufficient accuracy for this.

It will be appreciated that, to achieve that benefit, it is not necessary that the mounting features 18 are of a type (such as kinematic) to define the position and orientation of the article precisely within the machine operating volume by virtue of the interaction of the mounting features 18 with the holding device. Therefore, the at least one mounting feature may comprise kinematic mount features which engage with corresponding kinematic mount features on the holding device of the machine tool, but this is not essential. If such preformed initial kinematic mount features 18 are not provided, and if the location of the features being processed on the article 20 is important (as it is in this case), then an alternative process (e.g. a probing operation) could be used to determine the location of the article 20 within the machine tool's operating volume.

The invention claimed is:

1. A method of manufacturing an article, the method comprising:
    (a) performing an additive manufacturing process to form an article in an initial state, the article comprising kinematic mount features and the additive manufacturing process comprising forming the article, including the kinematic mount features, additively from a material according to a computer model of the article, such that the position of a predetermined feature on the article, relative to the kinematic mount features, is derivable from the computer model; and
    (b) performing a second manufacturing process to transform the article into a second state, the second manufacturing process comprising:
        (i) mounting, via the kinematic mount features formed during the additive manufacturing process, the article in a holding device of a machine for operating on the article, the position and orientation of the article in three linear and three rotational degrees of freedom within the machine operating volume being known and defined by the interaction of the kinematic mount features with the holding device; and
        (ii) with the article so mounted, processing the predetermined feature on the article using knowledge derived from the computer model of the position of the predetermined feature relative to the kinematic mount features.

2. A method as claimed in claim 1, wherein the article is supported during the additive manufacturing process by scaffolding on a lower side of the article, and the kinematic mount features are provided on a different side of the article free from the scaffolding.

3. A method as claimed in claim 1, wherein the article is formed layer-by-layer by the additive manufacturing process.

4. A method as claimed in claim 1, wherein the additive manufacturing process comprises a laser consolidation process.

5. A method as claimed in claim 1, wherein the additive manufacturing process comprises a laser sintering or laser melting process.

6. A method as claimed in claim 1, wherein the article is processed from multiple sides.

7. A method as claimed in claim 6, wherein the article is turned over during the second manufacturing process.

8. A method as claimed in claim 1, wherein processing the predetermined feature comprises finishing the predetermined feature.

9. A method as claimed in claim 1, wherein the predetermined feature is provided with excess material which is removed during the second manufacturing process.

10. A method as claimed in claim 1, wherein the kinematic mount features are formed on one side of the article.

11. A method as claimed in claim 1, wherein the article is supported during the additive manufacturing process by scaffolding on a lower side of the article, and the predetermined feature is processed on the article on the same side as the scaffolding.

12. A method as claimed in claim 11, wherein the predetermined feature is processed on the article during the second manufacturing process on a surface of the article on which the scaffolding is provided.

13. A method as claimed in claim 1, wherein the second manufacturing process comprises a subtractive process.

14. A method as claimed in claim 13, wherein the machine comprises a machine tool, and the second manufacturing process comprises machining at least a part of the article.

15. A method as claimed in claim 1, wherein the article comprises a plurality of products joined together, and the method further comprises subsequently separating the plurality of products from each other.

16. A method as claimed in claim 15, wherein the plurality of products comprise a plurality of dental restorations.

17. A method as claimed in claim 1, wherein the article comprises at least one product and at least one member on which the kinematic mount features are provided, and the method further comprises subsequently detaching the least one member from the at least one product.

18. A method as claimed in claim 17, wherein the at least one member comprises a central hub around which the at least one product is arranged.

19. A method as claimed in claim 17, wherein the article comprises a plurality of products joined together via the at least one member, and the method further comprises subsequently separating the plurality of products from each other.

20. A method as claimed in claim 17, wherein the kinematic mount features are formed on one side of the at least one member.

21. A method as claimed in claim 1, wherein the article comprises at least one dental restoration.

22. A method as claimed in claim 21, wherein the second manufacturing process comprises machining a part of the dental restoration that interfaces with a member in a mouth of a patient.

23. A method as claimed in claim 22, wherein the dental restoration comprises at least one portion for interfacing with an implant member and the second manufacturing process comprises machining the at least one portion for interfacing with the implant member.

* * * * *